(12) United States Patent
Dunagan

(10) Patent No.: US 8,868,216 B2
(45) Date of Patent: Oct. 21, 2014

(54) ELECTRODE GARMENT

(75) Inventor: Jay M. Dunagan, Wabasha, MN (US)

(73) Assignee: Covidien LP, Mansfield, MA (US)

( * ) Notice: Subject to any disclaimer, the term of this patent is extended or adjusted under 35 U.S.C. 154(b) by 211 days.

(21) Appl. No.: 12/432,142

(22) Filed: Apr. 29, 2009

(65) Prior Publication Data

US 2010/0130847 A1     May 27, 2010

Related U.S. Application Data

(60) Provisional application No. 61/116,748, filed on Nov. 21, 2008.

(51) Int. Cl.
| | |
|---|---|
| *A61N 1/02* | (2006.01) |
| *A61B 5/00* | (2006.01) |
| *A61B 5/0408* | (2006.01) |
| *A61N 1/04* | (2006.01) |
| *A61N 1/36* | (2006.01) |

(52) U.S. Cl.
CPC ........... *A61B 5/0408* (2013.01); *A61B 2562/02* (2013.01); *A61B 5/6804* (2013.01); *A61B 5/6805* (2013.01); *A61N 1/0456* (2013.01); *A61N 1/36014* (2013.01)
USPC .......................................... 607/149; 607/152

(58) Field of Classification Search
CPC ........................... A61N 1/0484; A61N 1/0492
USPC .......... 600/386, 388–390, 393; 607/149, 152, 607/153
See application file for complete search history.

(56) References Cited

U.S. PATENT DOCUMENTS

| | | | |
|---|---|---|---|
| 4,391,279 | A | 7/1983 | Stein |
| 4,537,198 | A | 8/1985 | Corbett |
| 4,580,572 | A | 4/1986 | Granek et al. |
| 4,583,547 | A | 4/1986 | Granek et al. |
| 4,583,549 | A | 4/1986 | Manoli |
| 4,608,987 | A | 9/1986 | Mills |
| 4,685,467 | A | 8/1987 | Cartmell et al. |
| 4,694,835 | A | 9/1987 | Strand |

(Continued)

FOREIGN PATENT DOCUMENTS

| | | |
|---|---|---|
| EP | 0 168 917 | 1/1986 |
| JP | 57-501216 | 7/1982 |

(Continued)

OTHER PUBLICATIONS

International Search Report and Written Opinion dated Jan. 20, 2010; 8 pages.

(Continued)

*Primary Examiner* — Carl H Layno
*Assistant Examiner* — Erica Lee
(74) *Attorney, Agent, or Firm* — Lisa E. Winsor, Esq.

(57) ABSTRACT

The present disclosure is directed to a wearable garment device for application of electrical current to a patient's tissue. The garment device includes a material having a aperture and a mesh material extending across the aperture. At least one electrode is attached onto one side of the mesh material. The surface of the mesh material attached to the at least one electrode is defined as the outer surface. The other surface of the mesh material is defined as the inner surface. The inner surface of the mesh material is placed against the patient's tissue to receive the electrical stimulation from the electrode.

23 Claims, 6 Drawing Sheets

(56) References Cited

U.S. PATENT DOCUMENTS

| | | | |
|---|---|---|---|
| 4,698,848 A | 10/1987 | Buckley |
| 4,700,710 A | 10/1987 | Hoffman |
| 4,709,702 A | 12/1987 | Sherwin |
| 4,729,377 A | 3/1988 | Granek et al. |
| 4,763,660 A | 8/1988 | Kroll et al. |
| 4,809,700 A | 3/1989 | Castelli |
| 4,832,608 A | 5/1989 | Kroll |
| 4,838,273 A | 6/1989 | Cartmell |
| 4,852,572 A | 8/1989 | Nakahashi et al. |
| 4,867,166 A | 9/1989 | Axelgaard et al. |
| 4,889,131 A | 12/1989 | Salem et al. |
| 4,911,169 A | 3/1990 | Ferrari |
| 4,928,696 A | 5/1990 | Henderson et al. |
| 4,967,038 A | 10/1990 | Gevins et al. |
| 4,996,989 A | 3/1991 | Stundel et al. |
| 5,016,636 A | 5/1991 | Kulakowski |
| 5,022,412 A | 6/1991 | Gracovetsky et al. |
| 5,038,796 A | 8/1991 | Axelgaard et al. |
| 5,042,481 A | 8/1991 | Suzuki et al. |
| 5,078,138 A | 1/1992 | Strand et al. |
| 5,119,816 A | 6/1992 | Gevins |
| 5,121,747 A | 6/1992 | Andrews |
| 5,169,380 A | 12/1992 | Brennan |
| 5,184,620 A | 2/1993 | Cudahy et al. |
| 5,224,479 A | 7/1993 | Sekine |
| 5,263,481 A | 11/1993 | Axelgaard |
| 5,313,942 A | 5/1994 | Platzker |
| 5,313,952 A | 5/1994 | Hoch |
| 5,341,806 A | 8/1994 | Gadsby et al. |
| 5,353,793 A | 10/1994 | Bornn |
| 5,356,428 A | 10/1994 | Way |
| 5,370,116 A | 12/1994 | Rollman et al. |
| 5,374,283 A | 12/1994 | Flick |
| 5,443,494 A | 8/1995 | Paolizzi et al. |
| 5,445,149 A | 8/1995 | Rotolo et al. |
| 5,450,845 A | 9/1995 | Axelgaard |
| 5,458,141 A | 10/1995 | Neil |
| 5,462,157 A | 10/1995 | Freeman et al. |
| 5,466,244 A | 11/1995 | Morgan |
| 5,479,934 A | 1/1996 | Imran |
| 5,487,759 A | 1/1996 | Bastyr et al. |
| 5,511,548 A | 4/1996 | Riazzi et al. |
| 5,518,007 A | 5/1996 | Becker |
| 5,617,853 A | 4/1997 | Morgan |
| 5,643,329 A | 7/1997 | Solomonow et al. |
| 5,645,062 A | 7/1997 | Anderson et al. |
| 5,645,063 A | 7/1997 | Straka, Jr. |
| 5,782,238 A | 7/1998 | Beitler |
| 5,785,040 A | 7/1998 | Axelgaard |
| 5,800,351 A | 9/1998 | Mann |
| 5,846,198 A | 12/1998 | Killmann |
| 5,868,671 A | 2/1999 | Mahoney |
| 5,871,534 A | 2/1999 | Messick et al. |
| 5,938,597 A | 8/1999 | Stratbucker |
| 6,032,060 A | 2/2000 | Carim et al. |
| 6,032,064 A | 2/2000 | Devlin et al. |
| 6,047,203 A | 4/2000 | Sackner et al. |
| 6,064,901 A | 5/2000 | Cartmell et al. |
| 6,065,154 A | 5/2000 | Hulings et al. |
| 6,067,464 A | 5/2000 | Musha |
| 6,134,480 A | 10/2000 | Minogue |
| 6,151,528 A | 11/2000 | Maida |
| 6,154,669 A | 11/2000 | Hunter et al. |
| 6,161,030 A | 12/2000 | Levendowski et al. |
| 6,178,357 B1 | 1/2001 | Gliner et al. |
| 6,198,955 B1 | 3/2001 | Axelgaard et al. |
| 6,219,568 B1 | 4/2001 | Kelly et al. |
| 6,259,939 B1 | 7/2001 | Rogel |
| 6,272,365 B1 | 8/2001 | Ronkainen et al. |
| 6,327,487 B1 | 12/2001 | Stratbucker |
| 6,341,229 B1 | 1/2002 | Akiva |
| 6,341,237 B1 | 1/2002 | Hurtado |
| 6,381,481 B1 | 4/2002 | Levendowski et al. |
| 6,381,482 B1 | 4/2002 | Jayaraman et al. |
| 6,393,317 B1 | 5/2002 | Fukuda et al. |
| 6,408,200 B1 | 6/2002 | Takashina |
| 6,418,333 B1 | 7/2002 | Axelgaard |
| 6,438,428 B1 | 8/2002 | Axelgaard et al. |
| 6,450,942 B1 | 9/2002 | Lapanashvili et al. |
| 6,453,203 B1 | 9/2002 | Yamazaki et al. |
| 6,456,872 B1 | 9/2002 | Faisandier |
| 6,477,397 B1 | 11/2002 | Ronkainen et al. |
| 6,480,731 B1 | 11/2002 | DeLuca et al. |
| 6,510,340 B1 | 1/2003 | Jordan |
| 6,532,379 B2 | 3/2003 | Stratbucker |
| 6,546,291 B2 | 4/2003 | Merfeld et al. |
| 6,551,252 B2 | 4/2003 | Sackner et al. |
| 6,553,247 B1 | 4/2003 | Rytky |
| 6,560,473 B2 | 5/2003 | Dominguez |
| 6,567,706 B2 | 5/2003 | Bar-Or et al. |
| 6,571,115 B2 | 5/2003 | Axelgaard et al. |
| 6,574,513 B1 | 6/2003 | Collura et al. |
| 6,600,942 B2 | 7/2003 | Nissiläet al. |
| 6,640,122 B2 | 10/2003 | Manoli et al. |
| 6,654,626 B2 | 11/2003 | Devlin et al. |
| 6,687,523 B1 | 2/2004 | Jayaramen et al. |
| 6,711,427 B1 | 3/2004 | Ketelhohn |
| 6,735,481 B1 | 5/2004 | Bingham et al. |
| 6,745,062 B1 | 6/2004 | Finneran et al. |
| 6,745,082 B2 | 6/2004 | Axelgaard |
| 6,755,795 B2 | 6/2004 | Marmaropoulos |
| 6,757,916 B2 | 7/2004 | Mah et al. |
| 6,775,566 B2 | 8/2004 | Nissila |
| 6,778,862 B2 | 8/2004 | Axelgaard et al. |
| 6,788,979 B1 | 9/2004 | Axelgaard et al. |
| 6,832,982 B1 | 12/2004 | Lapanashvili et al. |
| 6,840,955 B2 | 1/2005 | Ein |
| 6,847,836 B1 | 1/2005 | Sujdak |
| 6,850,791 B1 | 2/2005 | Axelgaard et al. |
| 6,915,148 B2 | 7/2005 | Finneran et al. |
| 6,917,825 B2 | 7/2005 | Finneran et al. |
| 6,952,605 B1 | 10/2005 | Scarberry |
| 6,970,731 B1* | 11/2005 | Jayaraman et al. ............ 600/388 |
| 6,973,344 B2 | 12/2005 | Finneran et al. |
| 7,027,877 B2 | 4/2006 | Dupelle et al. |
| 7,039,468 B2 | 5/2006 | Freed et al. |
| 7,062,309 B2 | 6/2006 | Ryu et al. |
| 7,069,089 B2 | 6/2006 | Minogue et al. |
| 7,072,721 B1 | 7/2006 | Trent |
| RE39,250 E | 8/2006 | Freeman et al. |
| 7,127,279 B2 | 10/2006 | Finneran et al. |
| 7,130,692 B2 | 10/2006 | Brighton et al. |
| 7,158,822 B2 | 1/2007 | Payne, Jr. |
| 7,177,705 B2 | 2/2007 | Cohen |
| 7,233,828 B2 | 6/2007 | Vlad |
| 7,254,447 B2 | 8/2007 | Campos et al. |
| 7,299,084 B1 | 11/2007 | Price |
| 7,315,754 B2 | 1/2008 | Leonhardt et al. |
| 2001/0044573 A1 | 11/2001 | Manoli et al. |
| 2002/0029005 A1 | 3/2002 | Levendowski et al. |
| 2002/0032475 A1 | 3/2002 | Arbel |
| 2002/0058982 A1 | 5/2002 | Axelgaard et al. |
| 2002/0068861 A1 | 6/2002 | Yang |
| 2002/0077688 A1 | 6/2002 | Kirkland |
| 2002/0077689 A1 | 6/2002 | Kirkland |
| 2002/0082491 A1 | 6/2002 | Nissila |
| 2002/0091313 A1 | 7/2002 | Feucht et al. |
| 2002/0123679 A1 | 9/2002 | Dominguez |
| 2002/0133069 A1 | 9/2002 | Roberts |
| 2002/0138125 A1 | 9/2002 | Axelgaard et al. |
| 2002/0143373 A1 | 10/2002 | Courtnage et al. |
| 2002/0151951 A1 | 10/2002 | Axelgaard et al. |
| 2002/0183605 A1 | 12/2002 | Devlin et al. |
| 2003/0045922 A1 | 3/2003 | Northrop |
| 2003/0120183 A1 | 6/2003 | Simmons |
| 2003/0158593 A1* | 8/2003 | Heilman et al. ............... 607/149 |
| 2003/0187341 A1 | 10/2003 | Sackner et al. |
| 2003/0212319 A1 | 11/2003 | Magill |
| 2004/0030270 A1 | 2/2004 | Johnson |
| 2004/0054273 A1 | 3/2004 | Finneran et al. |
| 2004/0054274 A1 | 3/2004 | Finneran et al. |
| 2004/0054275 A1 | 3/2004 | Finneran et al. |
| 2004/0054276 A1 | 3/2004 | Finneran et al. |
| 2004/0073271 A1 | 4/2004 | Harry et al. |

(56) References Cited

U.S. PATENT DOCUMENTS

| | | |
|---|---|---|
| 2004/0138546 A1 | 7/2004 | Reho et al. |
| 2004/0143313 A1 | 7/2004 | Chang et al. |
| 2004/0172115 A1 | 9/2004 | Miazga et al. |
| 2004/0210165 A1 | 10/2004 | Marmaropoulos et al. |
| 2004/0230226 A1 | 11/2004 | Bingham et al. |
| 2004/0236202 A1 | 11/2004 | Burton |
| 2004/0254624 A1 | 12/2004 | Johnson |
| 2004/0260166 A1 | 12/2004 | Merilainen |
| 2004/0260167 A1 | 12/2004 | Leonhardt et al. |
| 2004/0260376 A1 | 12/2004 | Craige, III et al. |
| 2005/0004489 A1 | 1/2005 | Sarkela et al. |
| 2005/0010096 A1 | 1/2005 | Blackadar |
| 2005/0010264 A1 | 1/2005 | Brighton et al. |
| 2005/0020935 A1 | 1/2005 | Helzel et al. |
| 2005/0054941 A1 | 3/2005 | Ting et al. |
| 2005/0090867 A1 | 4/2005 | Lapanashvili et al. |
| 2005/0113661 A1 | 5/2005 | Nazeri et al. |
| 2005/0124901 A1 | 6/2005 | Misczynski et al. |
| 2005/0137472 A1 | 6/2005 | Ryu et al. |
| 2005/0197556 A1 | 9/2005 | Stoler |
| 2005/0203591 A1 | 9/2005 | Brighton |
| 2005/0251003 A1 | 11/2005 | Istvan et al. |
| 2005/0277821 A1 | 12/2005 | Payne, Jr. |
| 2006/0084855 A1 | 4/2006 | Teschner et al. |
| 2006/0117805 A1 | 6/2006 | Valentine et al. |
| 2006/0135863 A1 | 6/2006 | Birnbaum et al. |
| 2006/0135884 A1 | 6/2006 | Hack et al. |
| 2006/0142654 A1 | 6/2006 | Rytky |
| 2006/0167353 A1 | 7/2006 | Nazeri |
| 2006/0190057 A1 | 8/2006 | Reese |
| 2006/0211934 A1 | 9/2006 | Hassonjee et al. |
| 2006/0234584 A1* | 10/2006 | Valentine ............... 442/304 |
| 2006/0247733 A1 | 11/2006 | Amer |
| 2006/0258914 A1 | 11/2006 | Derchak et al. |
| 2007/0010750 A1 | 1/2007 | Ueno et al. |
| 2007/0027387 A1 | 2/2007 | Fendrock |
| 2007/0038057 A1 | 2/2007 | Nam et al. |
| 2007/0038252 A1 | 2/2007 | Carroll |
| 2007/0049814 A1 | 3/2007 | Muccio |
| 2007/0073131 A1 | 3/2007 | Ryu et al. |
| 2007/0078324 A1 | 4/2007 | Wijisiriwardana |
| 2007/0083096 A1 | 4/2007 | Paradiso |
| 2007/0093706 A1 | 4/2007 | Gevins et al. |
| 2007/0106343 A1 | 5/2007 | Monogue et al. |
| 2007/0112262 A1 | 5/2007 | Payne, Jr. |
| 2007/0118032 A1 | 5/2007 | Finneran et al. |
| 2007/0225585 A1 | 9/2007 | Washbon et al. |
| 2007/0238945 A1 | 10/2007 | Delic et al. |
| 2007/0239212 A1 | 10/2007 | Schneider et al. |
| 2007/0293911 A1 | 12/2007 | Crowe et al. |
| 2008/0143080 A1 | 6/2008 | Burr |

FOREIGN PATENT DOCUMENTS

| | | |
|---|---|---|
| JP | 61-22839 | 1/1986 |
| JP | 2001-327610 | 11/2001 |
| WO | WO 82/00414 | 2/1982 |
| WO | WO 2010/059553 A1 | 5/2010 |

OTHER PUBLICATIONS

PCT International Preliminary Report on Patentability of the ISA; dated May 24, 2011; for PCT Pat. App. No. PCT/US2009/064540; 6 pages.

European Search Report; dated Mar. 20, 2013; for EP Pat. App. No. 09828072.0; 5 pages.

Response filed Oct. 7, 2013; to Communication dated Apr. 8, 2013; and European Search Report dated Mar. 20, 2013; for EP Pat. App. No. 09828072.0; 3 pages.

Japanese Notice of Reasons for Rejection dated Jan. 27, 2014; for Japanese Pat. App. Nio. 2011-537532; 7 pages.

Japanese Office Action (English translation) dated Jan. 27, 2014; for Japanese Pat. App. No. 2011-537532; 4 pages.

Japanese Office Action dated Jan. 27, 2014; for Japanese Pat. App. No. 2011-537532; 3 pages.

* cited by examiner

ELECTRODE GARMENT

CROSS-REFERENCE TO RELATED APPLICATIONS

The present application claims the benefit of, and priority to, U.S. Provisional Patent Application No. 61/116,748, filed Nov. 21, 2008, the entire content of which is incorporated by reference herein.

BACKGROUND

1. Technical Field

The present disclosure relates to a garment device containing at least one biomedical electrode.

2. Description of the Related Art

Biomedical electrodes are used to transmit electrical signals between the body of a patient and external medical equipment, such as a monitoring, diagnostic, or stimulating device.

Biomedical electrodes are commonly used in therapeutic and diagnostic medical applications, e.g., a variety of signal based rehabilitative procedures, electrocardiograph (ECG), or transcutaneous nerve stimulation (TENS) procedures, maternal and/or fetal monitoring. Conventional biomedical electrodes are secured to the skin of a patient via a hydrogel and/or pressure sensitive adhesive. An electrical cable of leadwire is used to place the electrode in communication with and external electrical source. Various mechanisms for connecting a male/female terminal of the electrode to the complementary male/female terminal of the leadwire typically include "snap on" connectors, "pinch clip" connectors, "pinch clip" arrangements, "twist on" couplings or magnetic couplings. A backside (i.e., a side opposite the hydrogel side) is typically provided with a non-conductive liner.

Transcutaneous electrical nerve stimulation (TENS) has been employed as a method to reduce pain or discomfort for mammalian patients. Typically, TENS electrodes deliver low voltage, low current electrical signals through the skin. In some electrotherapy devices, i.e., TENS devices, the electrical current may be pulsed and oscillatory.

Removal of biomedical electrodes from a patient's skin may often result in discomfort and irritation. Adhesion of the hydrogel to the patient's skin may result in irritation. Similarly, residual hydrogel on the skin after electrode removal may cause patient discomfort or irritation.

Electrotherapy devices typically comprise a source of electrical current attached to an electrode through one or more conducting wires. Monitoring devices typically comprise a system for detecting electrical current attached to a monitoring electrode through one or more conducting wires.

SUMMARY

The present disclosure is directed to a garment device for delivery of electrical current to a patient. The garment device includes a material member having an aperture and a non-conductive porous material, such as a mesh material or cotton cheesecloth, extending across the aperture. At least one electrode is attached onto one side of the mesh material. The surface of the mesh material attached to the at least one electrode is defined as the outer surface. The other surface of the mesh material is defined as the inner surface. The inside surface of the mesh material is placed against the patient's tissue.

A garment device having additional features will now be discussed. In some embodiments, the electrodes are held in a predetermined position on the mesh material by an adhesive layer applied to either the mesh material or to the electrode. A fastening mechanism for releasably connecting one end of the material member with another end of the material member may be included. The garment device may be in the form of a belt, a vest, or another wearable configuration. A flap may extend from the material member of the garment device to cover the inner surface or the outer surface of the mesh material. Multiple flaps may be used to cover both the inner surface and the outer surface of the mesh material. An envelope or pocket configured to support an energy delivery apparatus may be included as part of the garment device.

The mesh material may be constructed to allow transmission of the electrical current through the mesh material without substantial interference. The mesh material may also act as a conductor of the electrical current. The adhesive may penetrate through the mesh material and conduct the electrical current.

BRIEF DESCRIPTION OF THE DRAWINGS

Embodiments of the presently disclosed garment device are described herein with reference to the accompanying drawings, wherein.

Other features and advantages of the present disclosure will become apparent from the following detailed description, taken in conjunction with the accompanying drawings, which illustrate, by way of example, the principles of the present disclosure.

DETAILED DESCRIPTION OF EMBODIMENTS

The garment device of the present disclosure is directed to a garment for the application of therapeutic electrical stimulation to a patient. The current is supplied from a TENS electrode within the garment device that is in contact with an overlying mesh material. The mesh material provides an intermediate layer between the electrode and the tissue that allows the electrode to be placed either close to the tissue without being applied directly to the patient's tissue or to be placed in contact with the patient's tissue and have the mesh material interposed therebetween to facilitate removal of the electrode from the patient's tissue.

In the following disclosure, the garment device will be discussed as in the form of a belt, however, the garment device may also be in the form of a vest or other wearable article of clothing.

The garment device allows the electrode to have reduced adhesion to the tissue of the patient while allowing current to be delivered to the patient. Specifically, the garment device greatly reduces the time and effort required to apply and remove electrodes to the tissue, while reducing the presence of residual hydrogel, adhesives and the like, on the tissue once the electrode is removed. Irritation of the tissue as a result of the application of the electrode may also be minimized.

The mesh material may be constructed to allow transmission of the electrical current through the mesh material without substantial interference. The mesh material may also act as a conductor of the electrical current. The adhesive may penetrate through the mesh material and conduct the electrical current.

Figure 1:
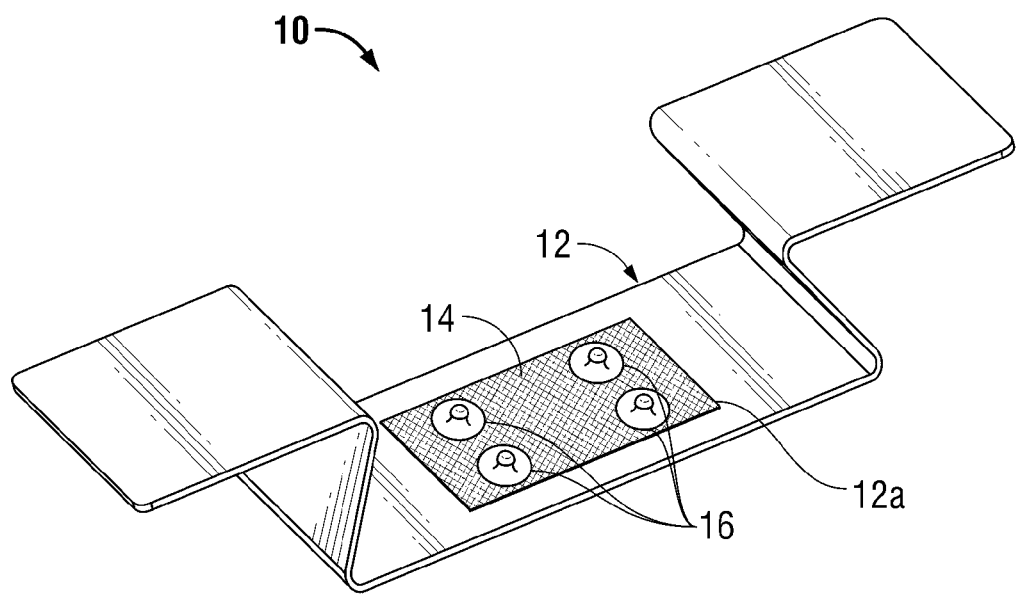
FIG. 1 is a perspective view of a garment device according to one embodiment the present disclosure.
Figure 2:
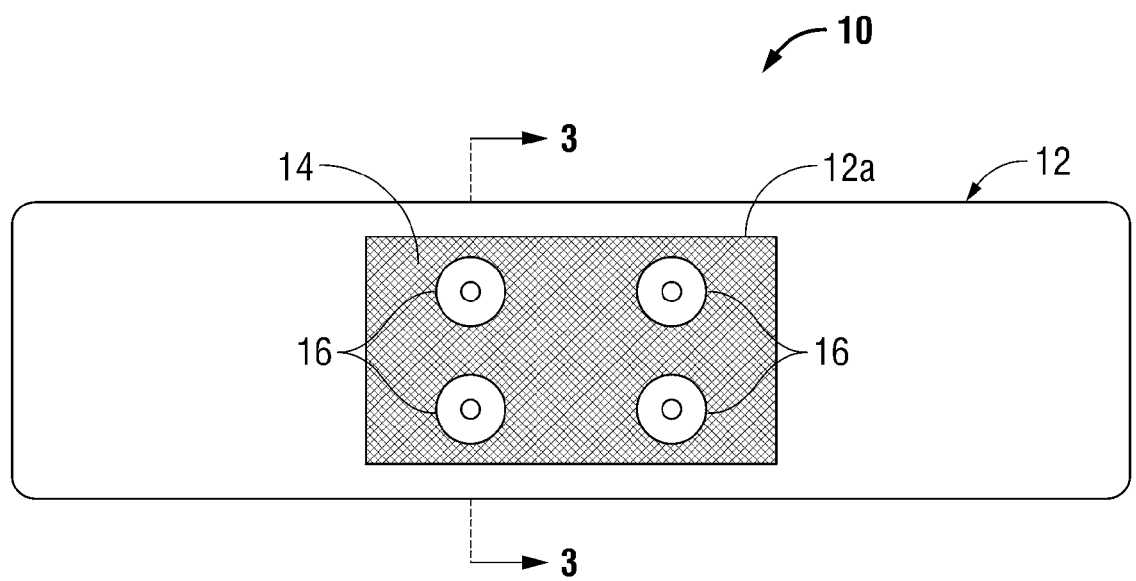
FIG. 2 is a plan view of the garment device in accordance with the embodiment of FIG. 1.
Figure 3:
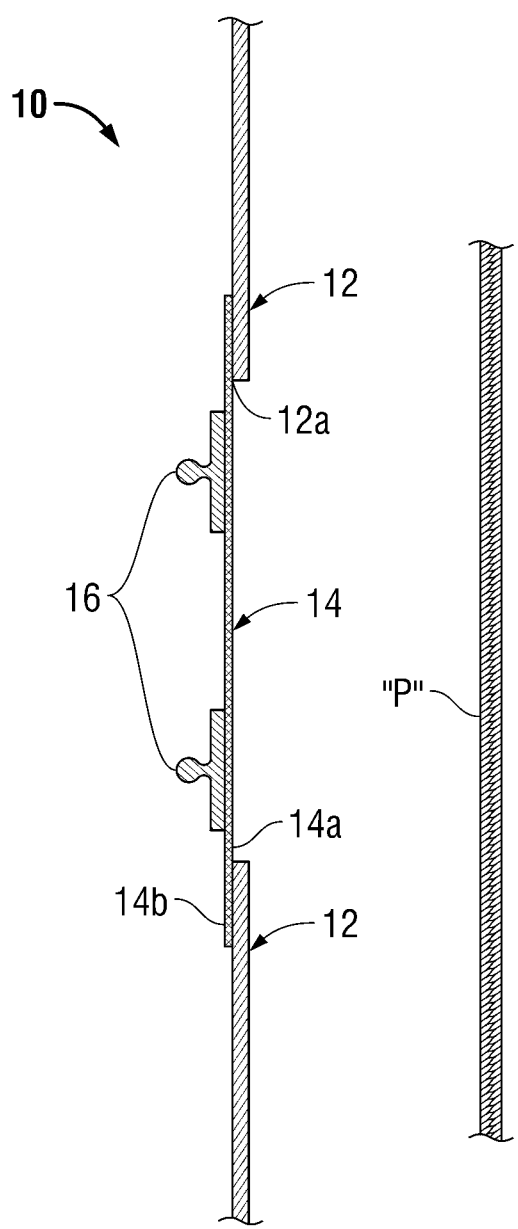
FIG. 3 is a cross-sectional view of the garment device in accordance with the embodiments of FIGS. 1 and 2, as taken through 3-3 of FIG. 2.

Referring now to the drawings, in which like reference numerals identify identical or substantially similar parts throughout the several views, FIGS. 1-3 illustrate a garment device 10 of the present disclosure for application of electrical current to a patient's tissue. The garment device 10 includes a material member 12 defining at least one aperture 12a formed therein. The material member 12 is a soft, thin, flexible material that holds to, conforms to, and supports the patient tissue and eliminates potential problems caused by movement or slippage once positioned. The flexible material may be a fabric, an elastomer, or a non-elastomer.

Garment device 10 includes a non-conductive porous material 14, such as a mesh material, cheesecloth or mesh fabric material, extending across aperture 12a and is attached about the periphery thereof. The mesh material 14 allows for easy removal from the patient. Mesh material 14 may be either permanently or removably attached to the inner surface or outer surface of material member 12.

As seen in FIG. 3, mesh material 14 includes a first side 14a of the mesh material 14. The surface that contacts the patient's tissue or first side of mesh material 14 is defined as the inner surface 14a, and opposite to the first side is defined as the outer surface 14b, As seen in FIG. 3, electrode 16 is disposed on second side or outer surface 14b of mesh material 14. In use, inner surface 14a of the mesh material is placed against the patient's tissue "P" that is to receive the electrical stimulation from the electrode 16. The electrode 16 may be removably attached to the outer surface 14a of the mesh material 14 by an adhesive.

Although the electrodes shown in the figures herein have a snap connection with respect to wearable garment device, any suitable electrode may be used, such as the electrodes disclosed in U.S. patent application Ser. No. 12/043,266, the disclosure of which is hereby incorporated by reference in their entirety.

Figure 4:
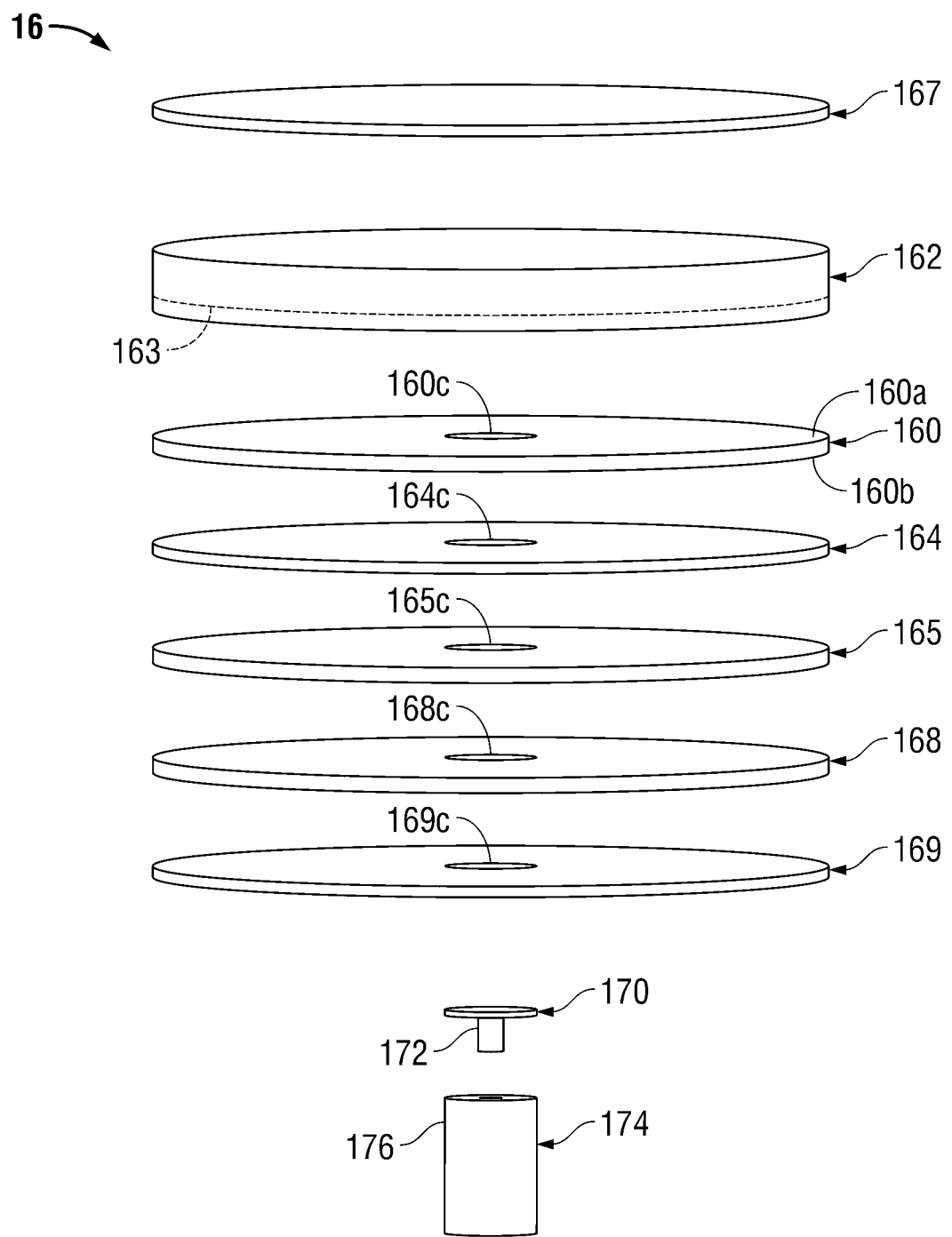
FIG. 4 is a perspective view of an exemplary electrode for use with the garment device of the present disclosure, shown with layers separated.

Referring now to FIG. 4, a snap style biomedical electrode 16 is configured for selective attachment or affixation to garment device 10. Electrode 16 includes a conductive member 160 defining a first or inner side 160a relative to the mesh material 14 and a second or outer side 160b, opposite first side 160a, Conductive member 160 may include a coating of a silver composition 164 on either or both the inner and outer sides 160a and 160b thereof, respectively (only silver composition 164 disposed on outer side 160b is shown).

Electrode 16 further includes a conductive composition 162 disposed adjacent inner side 160a of the conductive member 160 for application/adhesion to the mesh material 14. Conductive composition 162 includes a woven and/or nonwoven cloth or gauze material (e.g., scrim) 163 embedded therewithin or supporting the structure of the hydrogel. A first or inner side release liner 167 is releasably secured to conductive composition 162 to protect and/or preserve conductive composition 162 (e.g., the hydrogel) and is removed prior to application.

Electrode 16 further includes a reinforcement member 165, in the form of a scrim comprising a non-conductive fabric material, disposed adjacent outer side 160b of conductive member 160 and a layer of pressure sensitive adhesive (PSA) 168 disposed adjacent outer side 160b of conductive member 160. Pressure sensitive adhesive 168 overlies reinforcement member 165. A second release liner 169 is positioned to cover pressure sensitive adhesive 168.

Electrode 16 further includes a connector component 170 that defines a male terminal or male pin 172 and that is in electrical communication with at least conductive member 160 and to power supply or monitor (not shown). Electrical communication extends from connector component 170 through the conductive member 160 (and silver composition 164) and through conductive composition 162.

Each of silver composition 164, reinforcement member 165, pressure sensitive adhesive 168, and second release liner 169, may be provided with a respective aperture 164c, 165c, 168c, and 169c that is in general alignment with aperture 160c of conductive member 160 for accommodating pin 172.

The removable attachment or attachability of electrode 16 allows the electrode 16 to be removed, discarded, and replaced, as needed or instructed, in order to maintain longevity of the garment device 10. In use, as the garment device 10 is removed from the patient's tissue, the mesh material 14 spreads/distributes the removal forces from the electrode 16 to thereby reduce incidents of hydrogel or other adhesive from separating from the electrode 16 and remaining stuck to the patient's tissue. The garment device 10 may be cleaned by conventional processes to remove contaminants between uses or as required.

Figure 8:
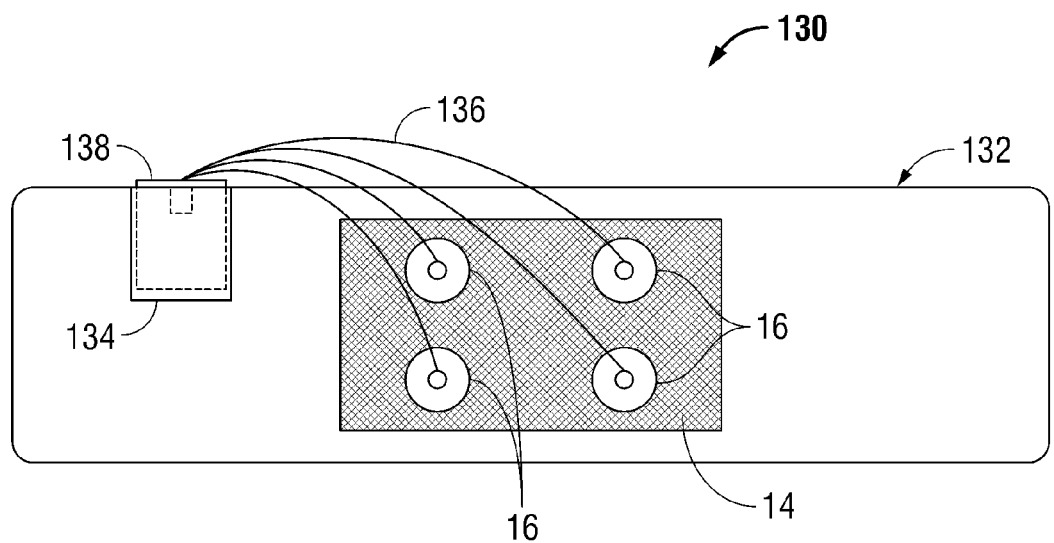
FIG. 8 is a plan view of the garment device in accordance with still another embodiment of the present disclosure.

In an alternative embodiment, it is contemplate that garment device 10 may be provided with multiple apertures 12a formed therein (as seen in FIG. 8), wherein each aperture accommodates a single or multiple electrodes 16.

Figure 5:
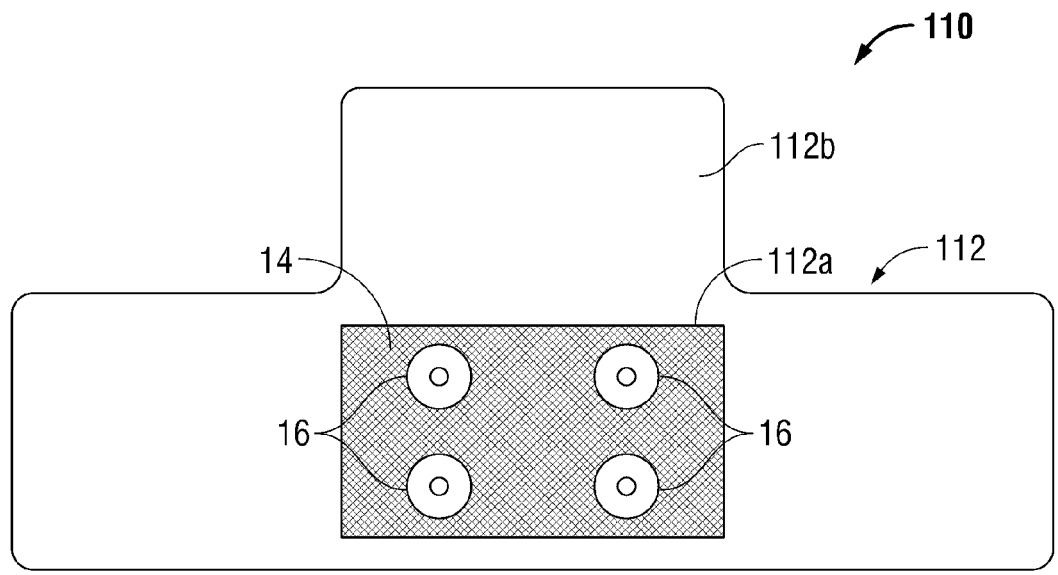
FIG. 5 is a plan view of the garment device in accordance with another embodiment of the present disclosure.

In another embodiment, shown in FIG. 5, garment device 110 has a material member 112 that includes a flap portion or protective cover 112b, The flap portion 112b may extend from the material member 112 to cover the inside surface of the mesh material 14 or the electrodes 16. The flap portion 112b can be used to protect the electrodes 16 and prevent electrical contact with undesirable surfaces. The flap portion 112b may also be used to prevent contaminants from contacting the mesh material 14. The flap portion 112b may also be a separate, entirely removable, cover, such as, for example, may comprise a wax coated paper, a foil, or other material that prevents external contaminants from contacting the mesh material 14 or other components of the garment device 110 contained under the flap portion 1 12b.

Figure 6:
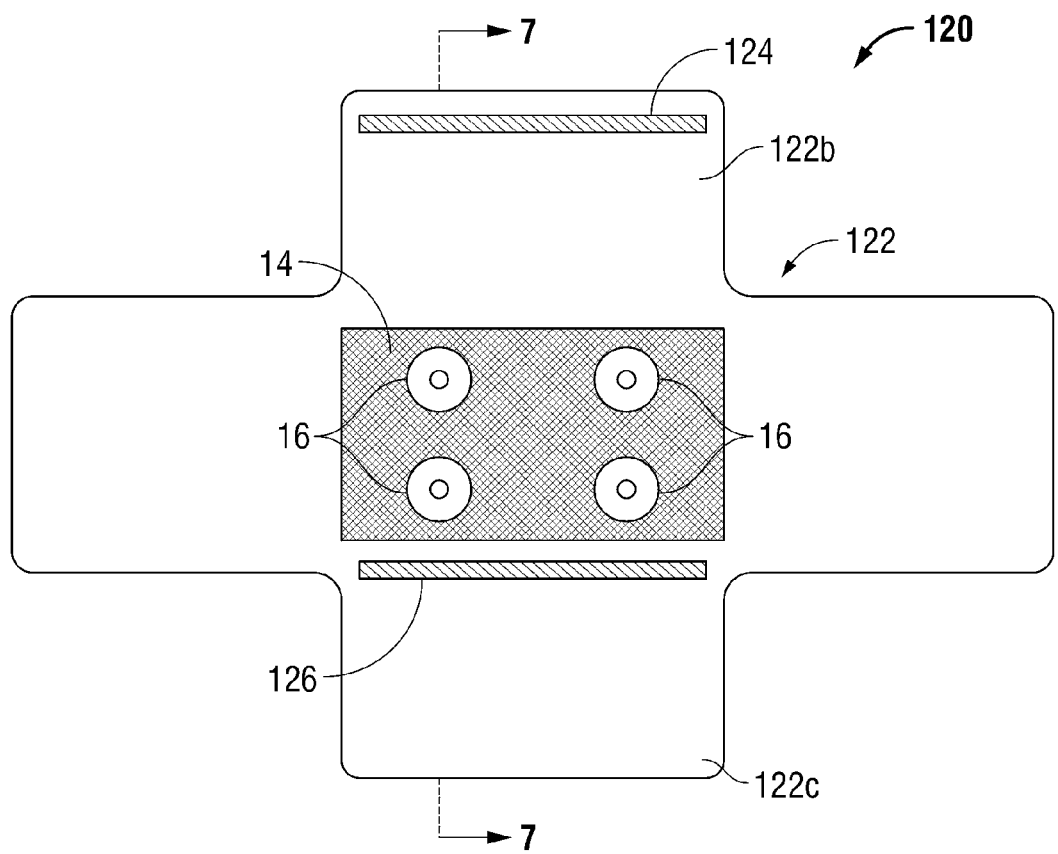
FIG. 6 is a plan view of the garment device in accordance with still another embodiment of the present disclosure.
Figure 7:
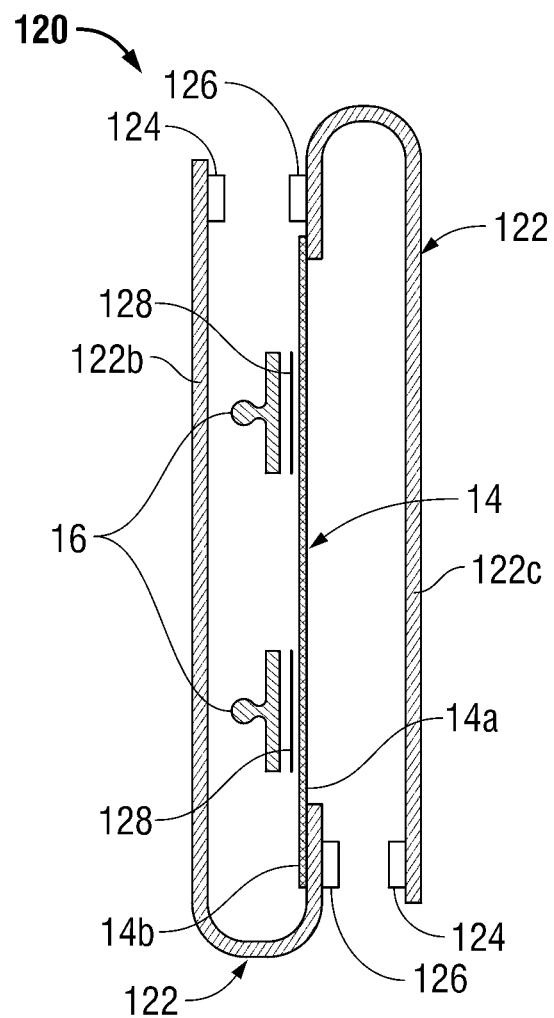
FIG. 7 is a cross-sectional view of the garment device in accordance with the embodiment of FIG. 5, as taken through 6-6 of FIG. 5.

In another embodiment, shown in FIG. 6, garment device 120 has a material member 122 that includes multiple flap portions 122b, 122c, Flap portions 122b, 122c may be used to cover both the outside/inside of the mesh material 14 and the electrodes 16. FIG. 7 illustrates one possible configuration of the material member 122 having multiple flap portions 122b, 122c, This configuration can utilize a two part fastener system 124 and 126 (e.g., hook and loop type fastener) to releasably engage the edge or perimeter of the flap portion 122b, 122c to another portion of the material member 122. As shown in FIG. 6, a first flap portion 122c is used to fold over and attach to an inside surface of the material member 122 and another or second flap portion 122b is used to fold over to protect the electrodes 16 and attach to an outer surface of the material member 122. The first flap portion 122c of material member 122 aids in the prevention of the mesh material 14 being contaminated or deformed.

The garment device 120 may be used with a single or multiple electrode(s) 16. Further, the electrodes 16 may be placed in virtually any configuration across the mesh material 14 to accommodate the particular patient's needs. A conductive layer 128 attaches and holds the electrodes 16 in position on the mesh material 14. The mesh material 14 spreads the removal forces of the garment device 120 and attached electrodes 16. The mesh material 14 reduces the incidents of remnants of the electrodes 16 on the patient's tissue once the garment device 120 is removed.

Other methods for maintaining the electrodes 16 in proper position are also envisioned, such as an additional placement flap having an area that allows the electrical connection of the electrode 16 to pass through the additional placement flap. Wherein the combinations of the electrical connection of the electrode acting upon the placement flap, and the sandwiching of the placement flap between the electrode and electrical connection maintain the electrode in place. Also envisioned is a system that allows the electrodes to be removable attached to a flap portion. This may be accomplished by such configurations as a hook and loop type fastener attached to both the electrode 16 and the flap portion or by an electrical connection (not shown) attached to the second flap portion and the electrode 16 being "snapped" into place.

In another embodiment, shown in FIG. 8, garment device 130 has a material member 132 that includes an envelope or pocket 134 formed therein, configured to support an energy delivery apparatus 138, and a series of connector leads 136 interconnecting energy delivery apparatus 138 and electrodes 16. This embodiment may be provided to the patient as a self-contained unit or kit that allows the patient to apply the electrical current on an as needed basis. The patient or operator would remove any flaps or protective covers over the mesh material 14 and place the garment device 130 about the tissue "P" (FIG. 3) to receive the electrical stimulation. The patient or operator would then activate the energy delivery apparatus 138 to start and stop the electrical stimulating current. Upon completion of the treatment, the patient or operator would remove the garment device and replace any flaps or protective covers. The garment device 130 could then be stored for future use.

Figure 9:
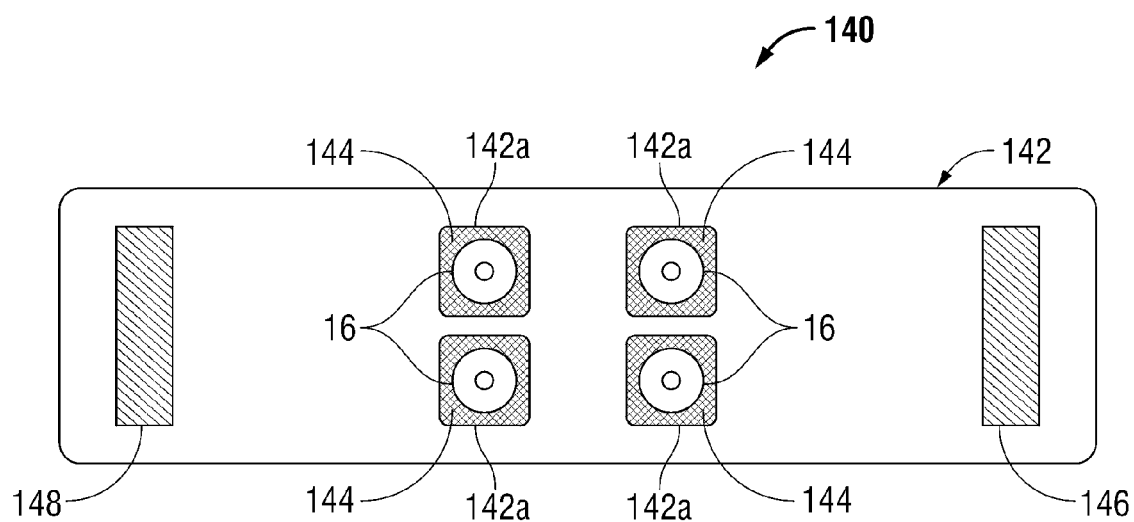
FIG. 9 is a plan view of the garment device in accordance with still another embodiment of the present disclosure.

In another embodiment, shown in FIG. 9, garment device 140 has a material member 142 that includes a fastening mechanism 146, 148 for releasably connecting one end of the material member with another end of the material member. Some of the various fastening mechanisms 146, 148 that may be used include, but are not limited to, magnets, hook and loop type fasteners, snaps, and buttons. The material member 142 also includes a series of apertures 142a, each having a mesh material 144 therewithin.

It will be understood that various modifications may be made to the embodiments of the presently disclosed garment device. Therefore, the above description should not be construed as limiting, but merely as exemplifications of embodiments. Those skilled in the art will envision other modifications within the scope and spirit of the present disclosure.

What is claimed is:

1. A garment device for application of electrical current to a patient's tissue, the garment device comprising:
    a material member defining an aperture therethrough and comprising a first fastener;
    an entirely non-conductive porous material extending across said aperture, the non-conductive porous material defining an inner surface facing toward the patient's tissue and an outer surface facing away from the patient's tissue; and
    at least one electrode placed along the outer surface of the non-conductive porous material; and
    a flap portion to cover the inner surface of the non-conductive porous material, the flap portion comprising a second fastener A garment device for application of electrical current to a patient's tissue, the garment device comprising:
    a garment comprising a first fastener and an entirely non-conductive porous material extending along a portion of the garment, the non-conductive porous material defining an inner surface facing toward the patient's tissue and an outer surface facing away from the patient's tissue;
    at least one replaceable electrode placed on the outer surface of the non-conductive porous material; and
    a flap portion to cover the inner surface of the non-conductive porous material, the flap portion comprising a second fastener that can engage with the first fastener to secure the flap portion in a closed position covering the inner surface of the non-conductive porous material;
    wherein the entirely non-conductive porous material is disposed between the electrode and the patient's tissue during use of the electrode so that, while the electrode is in use, the at least one electrode is in direct contact with the patient's tissue through the entirely non-conductive porous material and, upon removal of the garment device, removal forces are distributed by the non-conductive porous material;
    that can engage with the first fastener to secure the flap portion in a closed position;
    wherein the entirely non-conductive porous material is disposed between the electrode and the patient's tissue during use of the electrode so that, while the electrode is in use, the at least one electrode is in direct contact with the patient's tissue through the entirely non-conductive porous material and, upon removal of the garment device, removal forces are distributed by the non-conductive porous material.

2. The garment device of claim 1, wherein the material member is adapted to encircle at least a portion of the patient.

3. The garment device of claim 1, wherein the non-conductive porous material is a mesh material.

4. The garment device of claim 1, further comprising a second flap portion configured to fold over said outer surface of the non-conductive porous material.

5. The garment device of claim 1, further comprising an adhesive layer applied to at least one of the inner and outer surfaces of the non-conductive porous material.

6. The garment device of claim 1, further comprising an envelope configured to support an energy delivery apparatus.

7. The garment device of claim 4, wherein the second flap portion is configured to fold over said outer surface of the non-conductive porous material and the at least one electrode positioned on the outer surface of the non-conductive porous material.

8. The garment device of claim 1, wherein the non-conductive porous material is removably attachable to the material member.

9. The garment device of claim 1, wherein the at least one electrode includes at least a pair of electrodes placed along the outer surface of the non-conductive porous material.

10. A garment device for application of electrical current to a patient's tissue, the garment device comprising:

a garment comprising a first fastener and an entirely non-conductive porous material extending along a portion of the garment, the non-conductive porous material defining an inner surface facing toward the patient's tissue and an outer surface facing away from the patient's tissue;

at least one replaceable electrode placed on the outer surface of the non-conductive porous material; and a flap portion to cover the inner surface of the non-conductive porous material, the flap portion comprising a second fastener that can engage with the first fastener to secure the flap portion in a closed position to cover the inner surface of the non-conductive porous material;

wherein the entirely non-conductive porous material is disposed between the electrode and the patient's tissue during use of the electrode so that, while the electrode is in use, the at least one electrode is in direct contact with the patient's tissue through the entirely non-conductive porous material and, upon removal of the garment device, removal forces are distributed by the non-conductive porous material.

11. The garment device of claim 10, wherein the garment is constructed from a fabric.

12. The garment device of claim 10, wherein the non-conductive porous material is a mesh material.

13. The garment device of claim 10, wherein the garment is configured to hold the at least one replaceable electrode in place.

14. The garment device of claim 10, wherein the electrode includes a hydrogel and is positioned such that the hydrogel is in contact with the non-conductive porous material.

15. The garment device of claim 10, wherein the garment further comprises an envelope configured to support an energy delivery apparatus.

16. The garment device of claim 10, wherein the at least one replaceable electrode further comprises an adhesive material on both an inner surface and an outer surface thereof.

17. The garment device of claim 10, wherein the non-conductive porous material is removably attachable to the garment.

18. The garment device of claim 10, wherein the at least one replaceable electrode includes at least a pair of replaceable electrodes placed on the outer surface of the non-conductive porous material.

19. A garment device for application of electrical current to a patient's tissue, the garment device comprising:

a material member defining an aperture therethrough;

a first fastener attached to the material member;

an entirely non-conductive porous material extending across said aperture, the nonconductive porous material defining an inner surface facing toward the patient's tissue and an outer surface facing away from the patient's tissue;

a flap portion to cover the inner surface of the nonconductive porous material, the flap portion comprising a second fastener that can engage with the first fastener to secure the flap portion in a closed position to cover the inner surface; and at least one electrode detachably located on the outer surface of the non-conductive porous material;

wherein the entirely non-conductive porous material is disposed between the electrode and the patient's tissue during use of the electrode so that, while the electrode is in use, the at least one electrode is in direct contact with the patient's tissue through the entirely non-conductive porous material and, upon removal of the garment device, removal forces are distributed by the non-conductive porous material.

20. The garment device of claim 19, wherein the non-conductive porous material is a mesh material.

21. The garment device of claim 19, wherein the material member has at least a second flap portion configured to cover the outer surface of the non-conductive porous material.

22. The garment device of claim 19, wherein the non-conductive porous material is removably attachable to the material member.

23. The garment device of claim 19, wherein the at least one electrode includes at least a pair of electrodes detachably located between the material member and the outer surface of the non-conductive porous material.

* * * * *